United States Patent
Hayashi

(10) Patent No.: US 8,536,343 B2
(45) Date of Patent: Sep. 17, 2013

(54) ARYLAMIDINE DERIVATIVE, SALT THEREOF AND ANTIFUNGAL AGENT CONTAINING THOSE

(75) Inventor: Kazuya Hayashi, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 1002 days.

(21) Appl. No.: 12/159,527

(22) PCT Filed: Dec. 27, 2006

(86) PCT No.: PCT/JP2006/326061
§ 371 (c)(1),
(2), (4) Date: Jun. 27, 2008

(87) PCT Pub. No.: WO2007/074868
PCT Pub. Date: Jul. 5, 2007

(65) Prior Publication Data
US 2010/0016602 A1     Jan. 21, 2010

(30) Foreign Application Priority Data
Dec. 29, 2005 (JP) .................................. 2005-380547

(51) Int. Cl.
*A61K 31/445* (2006.01)
*C07D 211/26* (2006.01)

(52) U.S. Cl.
USPC .......................................... 546/231; 514/331

(58) Field of Classification Search
USPC .......................................... 546/231; 514/331
See application file for complete search history.

(56) References Cited

U.S. PATENT DOCUMENTS

| | | | |
|---|---|---|---|
| 6,153,613 A | 11/2000 | Ono et al. | |
| 6,503,940 B2 * | 1/2003 | Boykin et al. | 514/422 |
| 7,291,617 B2 * | 11/2007 | Hayashi et al. | 514/252.1 |
| 7,700,623 B2 * | 4/2010 | Hayashi et al. | 514/317 |
| 2003/0130265 A1 | 7/2003 | Pouzet et al. | |
| 2005/0113424 A1 | 5/2005 | Hayashi et al. | |
| 2009/0087480 A1 | 4/2009 | Nomura et al. | |

FOREIGN PATENT DOCUMENTS

| | | |
|---|---|---|
| EP | 1 481 966 A1 | 12/2004 |
| EP | 1 767 526 A1 | 3/2007 |
| JP | 8 231515 | 9/1996 |
| JP | 2005 97298 | 4/2005 |
| WO | WO 00/67751 | 11/2000 |
| WO | 03 074476 | 9/2003 |
| WO | 2006 003881 | 1/2006 |
| WO | WO 2006/109642 A1 | 10/2006 |

OTHER PUBLICATIONS

Weller et. al. "Orally Active Fibrinogen Receptor Antagonists. 2. Amidoximes as Prodrugs of Amidines" Journal of Medicinal Chemistry 1996, 39, 3139-3147.*
U.S. Appl. No. 12/433,750, filed Mar. 31, 2009, Nishikawa.
U.S. Appl. No. 11/631,399, filed Dec. 29, 2006, Hayashi, et al.

* cited by examiner

*Primary Examiner* — David K O Dell
(74) *Attorney, Agent, or Firm* — Oblon, Spivak, McClelland, Maier & Neustadt, L.L.P.

(57) ABSTRACT

Disclosed is an arylamidine derivative represented by the following general formula:

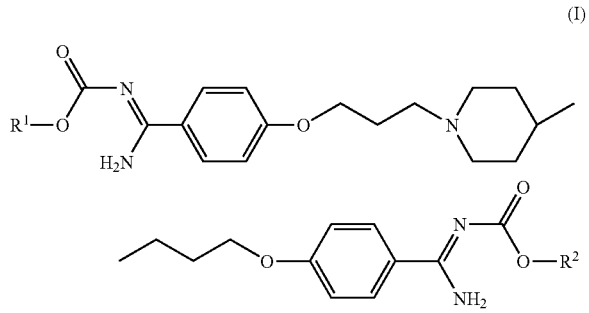

(wherein $R^1$ and $R^2$ independently represent an optionally substituted $C_{3-4}$ alkyl group) or a salt thereof, which is useful as an antifungal agent.

3 Claims, No Drawings

ARYLAMIDINE DERIVATIVE, SALT THEREOF AND ANTIFUNGAL AGENT CONTAINING THOSE

CROSS-REFERENCE TO RELATED APPLICATIONS

This application is a 371 of PCT/JP06/32061 filed Dec. 27, 2006 and claims the benefit of JP 2005-380547 filed Dec. 29, 2005.

TECHNICAL FIELD

The present invention relates to a novel arylamidine derivative and salt thereof having antifungal activity, and an antifungal agent comprising the same as an active ingredient.

BACKGROUND ART

Serious deep mycosis such as invasive candidiasis can be often a fatal disease. It has been considered that a principal defense mechanism of a host organism against fungi such as *candida* originally owes to nonspecific immunity by neutrophils. So long as this defense mechanism functions normally, the risk of infection by fungi is limited. However, in recent years, the risk of developing deep mycosis has increased due to an increase in the number of patients with underlying diseases compromising the immune system of the organism, such as malignant tumors or AIDS, overuse of anticancer drugs or immunosuppressive drugs, heavy use of antibacterial antibiotic substances or steroid hormones and long-term use of intravenous hyperalimentation or venous catheterization (Non-Patent Document 1).

Only 7 agents for such deep mycosis are known, namely, amphotericin B, flucytosine, miconazole, fluconazole, itraconazole, micafungin and voriconazole. Amphotericin B has very strong fungicidal action, but its clinical use is limited due to a problem of side effects, for example, nephrotoxicity. Flucytosine has a problem of development of tolerance and is rarely used alone today. Micafungin has weak activity against *Cryptococcus* spp. Other agents are generically called azole antifungal agents and are most frequently used now owing to the favorable balance between efficacy and safety, although their fungicidal actions tend to be in general inferior to that of amphotericin B (Non-Patent Document 2).

Recently, fluconazole-resistant *Candida albicans* have been detected at high frequency derived from oropharyngeal candidiasis of AIDS patients, who have received repeated-dose administration of fluconazole. Furthermore, many of the resistant strains show cross-resistance to itraconazole and other azole agents. Further, isolation of resistant strains from non-AIDS patients, who have developed chronic mucocutaneous candidiasis or deep candidiasis, has been reported (Non-Patent Document 3). The issue of the resistance has a serious impact on management of rapidly increasing patients with deep mycosis (Non-Patent Document 3).

On the other hand, an arylamidine derivative having an antifungal activity is known (Patent Documents 1 and 2).
Patent Document 1: WO-A-03-074476
Patent Document 2: WO-A-2006-003881
Non-Patent Document 1: Rinsho to Biseibutsu (Clinics and Microorganisms), vol. 17, p. 265-266, 1990
Non-Patent Document 2: Rinsho to Biseibutsu (Clinics and Microorganisms), vol. 21, p. 277-283, 1994
Non-Patent Document 3: Rinsho to Biseibutsu (Clinics and Microorganisms), vol. 28, p. 51-58, 2001

DISCLOSURE OF THE INVENTION

An antifungal agent has been strongly desired, which works based on a different mechanism of action from those of existing agents, is effective against azole-agent-resistant fungi, has few side-effects and is well absorbed orally.

Under such circumstances, the present inventors have intensively studied and have found that an arylamidine derivative represented by the general formula [1] or a salt thereof:

[Formula 1]

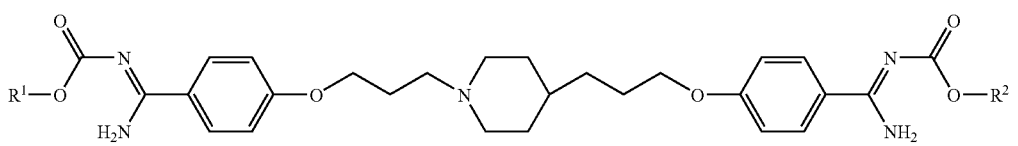

[1]

(wherein $R^1$ and $R^2$ identically or differently represent an optionally substituted $C_{3-4}$ alkyl group) is superior in oral absorption, effective against azole-agent-resistant fungi, and has reduced side-effects, thereby completing the present invention.

EFFECT OF THE INVENTION

Compounds of the present invention have strong activity against fungi including azole-agent-resistant fungi, are superior in oral absorption, have reduced interaction with other agents, are highly safe and useful as an antifungal agent.

BEST MODE FOR CARRYING OUT THE INVENTION

The present invention is described below in more detail.
In the present description, unless otherwise specified, a halogen atom means a fluorine atom, a chlorine atom, a bromine atom and an iodine atom; a lower alkyl group means a straight-chain or branched-chain $C_{1-6}$ alkyl group such as methyl, ethyl, propyl, isopropyl, butyl, sec-butyl, isobutyl, tert-butyl, pentyl and isopentyl; a $C_{3-4}$ alkyl group means propyl, isopropyl, butyl, sec-butyl, isobutyl and tert-butyl group; an aralkyl group means an ar-$C_{1-6}$ alkyl group such as benzyl, diphenylmethyl, trityl, phenethyl and naphthylmethyl; an alkoxyalkyl group means a $C_{1-6}$ alkyloxy-$C_{1-6}$ alkyl group such as methoxymethyl and 1-ethoxyethyl; an aralkyloxyalkyl group means an ar-$C_{1-6}$ alkyloxy-$C_{1-6}$ alkyl group such as benzyloxymethyl and phenethyloxymethyl;

an alkanesulfonyl group means a $C_{1-6}$ alkanesulfonyl group such as methanesulfonyl, ethanesulfonyl and propanesulfonyl; an arylsulfonyl group means, for example, benzenesulfonyl, toluenesulfonyl and naphthalenesulfonyl group;

an alkanesulfonyloxy group means a $C_{1-6}$ alkanesulfonyloxy group such as methanesulfonyloxy and ethanesulfonyloxy; an arylsulfonyloxy group means, for example, benzenesulfonyloxy and toluenesulfonyloxy group;

an acyl group means, for example, a formyl group, a straight-chain or branched-chain $C_{2-12}$ alkanoyl group such as acetyl, propionyl and isovaleryl, an ar-$C_{1-6}$ alkylcarbonyl group such as benzylcarbonyl, an aroyl group such as benzoyl and naphthoyl, a heterocyclic carbonyl group such as nicotinoyl, thenoyl, pyrrolidinocarbonyl and furoyl, a carboxy-$C_{1-6}$ alkylcarbonyl group such as 3-carboxypropanoyl and 4-carboxybutanoyl, a $C_{1-6}$ alkyloxycarbonyl $C_{1-6}$ alkylcarbonyl group such as 3-(methoxycarbonyl)propanoyl and 4-(methoxycarbonyl)butanoyl, a succinyl group, a glutaryl group, a maleoyl group, a phthaloyl group and a straight-chain or branched-chain α-aminoalkanoyl group whose N-terminus is optionally protected and which is derived from an amino acid (examples of the amino acid include: glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline);

an alkyloxycarbonyl group means a straight-chain or branched-chain $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group means an ar-$C_{1-6}$ alkyloxycarbonyl group such as benzyloxycarbonyl and phenethyloxycarbonyl; an aryloxycarbonyl group means a phenyloxycarbonyl group; an oxygen-containing heterocyclic group means a group such as tetrahydrofuryl and tetrahydropyranyl; a heterocyclic oxycarbonyl group means a group such as 2-furfuryloxycarbonyl and 8-quinolyloxycarbonyl; a substituted silyl group means, for example, a group such as trimethylsilyl, triethylsilyl and tributylsilyl.

Each of the aforementioned groups is further optionally substituted by one or more groups selected from a halogen atom, a hydroxyl group, a carboxyl group and a lower alkyl group.

An amino protecting group includes all conventional groups which are usable as a protecting group for an amino group, for example, an acyl group, an alkyloxycarbonyl group, an aralkyloxycarbonyl group, an aryloxycarbonyl group, an aralkyl group, an alkoxyalkyl group, an aralkyloxyalkyl group, an alkanesulfonyl group, an arylsulfonyl group and a substituted silyl group.

A hydroxyl protecting group includes all conventional groups which are usable as a protecting group for a hydroxyl group, for example, an acyl group, an alkyloxycarbonyl group, an aralkyloxycarbonyl group, a heterocyclic oxycarbonyl group, an aralkyl group, an oxygen-containing heterocyclic group, an alkoxyalkyl group, an aralkyloxyalkyl group, an alkanesulfonyl group, an arylsulfonyl group and a substituted silyl group.

A leaving group includes, for example, a halogen atom, an alkanesulfonyloxy group and an arylsulfonyloxy group.

A salt of the compound of the general formula [1] includes, for example, a salt with a mineral acid such as hydrochloric acid, hydrobromic acid, phosphoric acid and sulfuric acid; a salt with an organic carboxylic acid such as formic acid, trichloroacetic acid, L-tartaric acid, maleic acid, fumaric acid and trifluoroacetic acid; and a salt with a sulfonic acid such as methanesulfonic acid, benzenesulfonic acid, p-toluenesulfonic acid, mesitylenesulfonic acid and naphthalenesulfonic acid.

A preferable salt of the compound of the general formula [1] includes a pharmacologically acceptable salt.

A possible substituent for an optionally substituted $C_{3-4}$ alkyl group of $R^1$ and $R^2$ includes a halogen atom, a hydroxyl group and a carboxyl group.

A preferable compound of the present invention includes the following compounds:

the compound, in which $R^1$ is preferably a $C_{3-4}$ alkyl group, more preferably a propyl, isopropyl or butyl group, and further preferably a butyl group;

the compound, in which $R^2$ is preferably a $C_{3-4}$ alkyl group, more preferably a propyl, isopropyl or butyl group, and further preferably a butyl group;

the compound, in which $R^1$ and $R^2$ are identical, is preferable.

A method for producing compounds of the present invention is described.

Compounds of the present invention may be produced by combining per se publicly known methods, for example, by the following production method.

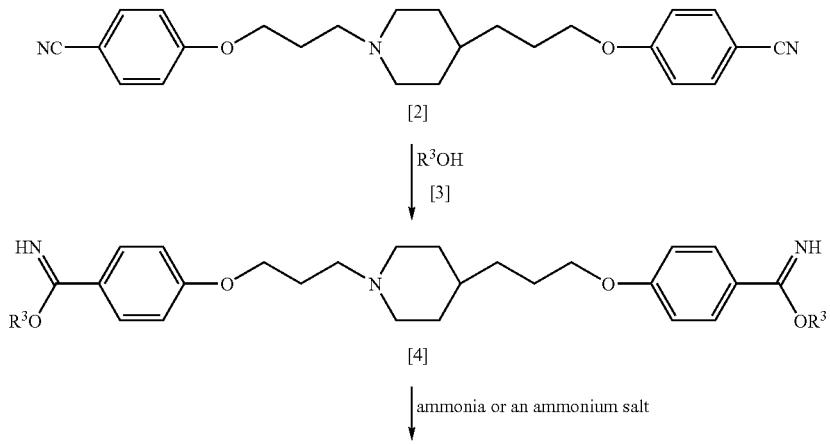

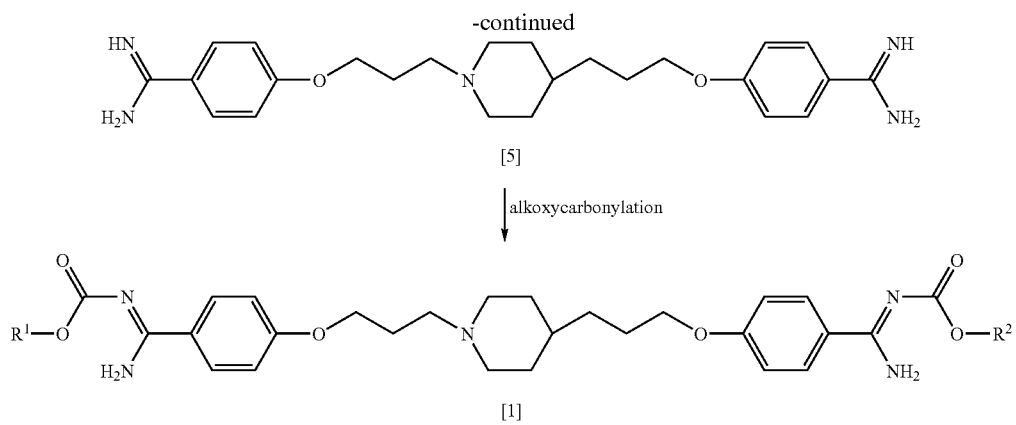

[5]

↓ alkoxycarbonylation

[1]

wherein $R^3$ represents a lower alkyl group; and $R^1$ and $R^2$ are as defined above.

(1-1)

The compound of the general formula [4] may be produced by reacting the compound of the formula [2] with the compound of the general formula [3] in the presence of an acid.

A solvent used in the reaction is not particularly restricted, insofar as it does not adversely affect the reaction. Examples of the solvent include: alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; sulfoxides such as dimethyl sulfoxide; ketones such as acetone and 2-butanone; esters such as ethyl acetate; and carboxylic acids such as acetic acid. These solvents may be used in combination. The compound of the general formula [3] may be used as a solvent.

Examples of an acid used in the reaction include hydrogen chloride, hydrogen bromide, perchloric acid, p-toluenesulfonic acid and methanesulfonic acid. Such an acid may be used by 1 to 200-fold moles, preferably 5 to 100-fold moles, for the amount of the compound of the formula [2].

In the reaction, the amount of the compound of the general formula [3] used may be 2 to 1000-fold moles for the amount of a compound of the formula [2], and the compound of the general formula [3] is preferably used as a solvent.

The reaction may be carried out at −30 to 150° C., preferably at 10 to 50° C. for 30 minutes to 24 hours.

(1-2)

The compound of the formula [5] may be produced by reacting the compound of the general formula [4] with ammonia or an ammonium salt.

A solvent used in the reaction is not particularly restricted, insofar as it does not adversely affect the reaction. Examples of the solvent include: alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitriles such as acetonitrile; sulfoxides such as dimethyl sulfoxide; heteroaromatics such as pyridine; and water. These solvents may be used in combination.

Examples of an ammonium salt include, for example, ammonium chloride, ammonium bromide and ammonium acetate. The amount of ammonia or an ammonium salt used may be 3 to 100-fold moles, preferably 3 to 10-fold moles, for the amount of the compound of the general formula [4].

The reaction may be carried out at 0 to 150° C., preferably at 20 to 120° C. for 1 minute to 24 hours.

(1-3)

The compound of the general formula [1] may be produced by subjecting the compound of the formula [5] to an alkoxycarbonylation reaction with a reactive derivative in the presence or absence of a base.

A solvent used in the reaction is not particularly restricted, insofar as it does not adversely affect the reaction. Examples of the solvent include: amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethylether, diethylene glycol diethylether and ethylene glycol monomethyl ether; nitriles such as acetonitrile; sulfoxides such as dimethyl sulfoxide; ketones such as acetone, methyl isobutyl ketone and 2-butanone; esters such as ethyl acetate; carboxylic acids such as acetic acid; heteroaromatics such as pyridine; and water. These solvents may be used in combination.

Examples of the reactive derivative include: esters of chloroformic acid such as propyl chloroformate, isopropyl chloroformate, butyl chloroformate and isobutyl chloroformate; and active esters such as 4-nitrophenyl propyl carbonate, 4-nitrophenyl isopropyl carbonate, butyl 4-nitrophenyl carbonate, isobutyl 4-nitrophenyl carbonate, propyl 1H-imidazole-1-carboxylate, butyl 1H-imidazole-1-carboxylate, isopropyl 1H-imidazole-1-carboxylate and isobutyl 1H-imidazole-1-carboxylate. These reactive derivatives may be used without isolation after preparation in the reaction system.

Examples of a base, which may be optionally used in the reaction, include: metal alkoxides such as sodium methoxide, sodium ethoxide, potassium tert-butoxide and sodium tert-butoxide; inorganic bases such as sodium hydroxide, potassium hydroxide, sodium bicarbonate, sodium carbonate, potassium carbonate, sodium hydride and potassium hydride; and organic bases such as triethylamine, N,N-diisopropylethylamine, 1,8-diazabicyclo-[5.4.0]-undec-7-ene (DBU) and pyridine.

The amount of the reactive derivative and the base used may be 2 to 100-fold moles, preferably 2 to 10-fold moles, for the amount of the compound of the formula [5].

The reaction may be carried out at −20 to 100° C., preferably at 20 to 80° C. for 1 minute to 24 hours.

12, p. 1203-1208 (2002), etc. Then, the compound of the formula [5] may be alkoxycarbonylated to produce the compound of the general formula [1].

Next, a series of the reactions is described below in more detail.

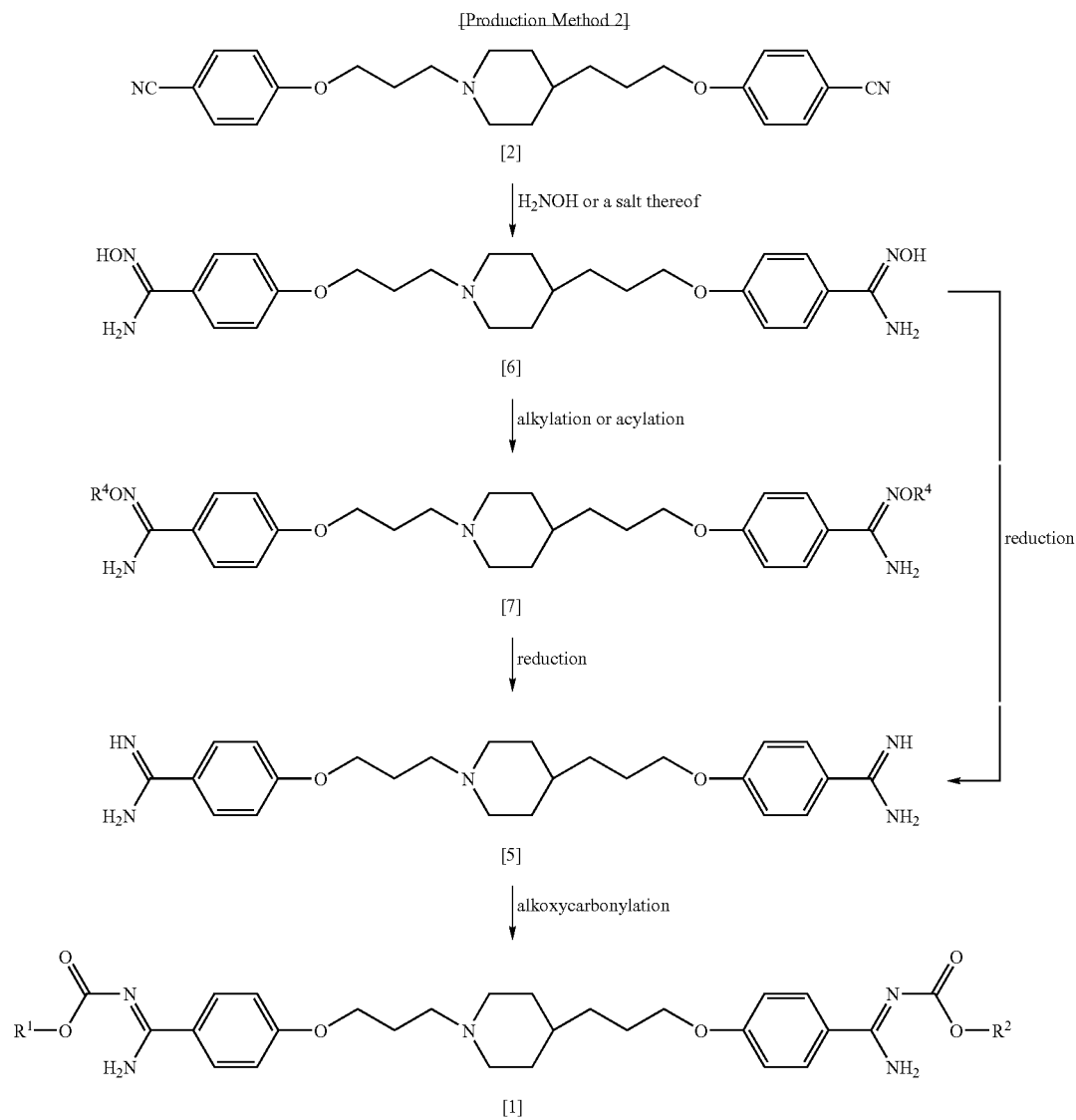

wherein $R^4$ represents an acyl, lower alkyl or aralkyl group which is optionally substituted; and $R^1$ and $R^2$ are as defined above.

The compound of the formula [6] may be produced from the compound of the formula [2]. Next, the compound of the formula [6] may be alkylated or acylated to produce the compound of the general formula [7]. Further, by reducing the compound of the formula [6], the compound of the formula [5] may be produced. The compound of the formula [5] may also be produced by reducing the compound of the general formula [7]. These reactions may be conducted in accordance with, or based on methods described in Tetrahedron, vol. 51, p. 12047-12068 (1995); Synthetic Communication, vol. 26, p. 4351-4367 (1996); Synthesis, vol. 16, p. 2467-2469 (2003); Heterocycles, vol. 60, p. 1133-1145 (2003); and Bioorganic and Medicinal Chemistry Letter, vol.

(2-1)

The compound of the formula [6] may be produced by reacting the compound of the formula [2] with hydroxylamine or its salt in the presence or absence of a base.

A solvent used in the reaction is not particularly restricted, insofar as it does not adversely affect the reaction. Examples of the solvent include: alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; sulfoxides such as dimethyl sulfoxide;

ketones such as acetone and 2-butanone; heteroaromatics such as pyridine; and water. These solvents may be used in combination.

Examples of a base, which may be optionally used in the reaction, include: metal alkoxides such as sodium methoxide, sodium ethoxide, potassium tert-butoxide and sodium tert-butoxide; inorganic bases such as sodium hydroxide, potassium hydroxide, sodium bicarbonate, sodium carbonate, potassium carbonate, sodium hydride and potassium hydride; and organic bases such as triethylamine and pyridine.

The amount of the base used may be 2 to 100-fold moles, preferably 2 to 20-fold moles, for the amount of the compound of the formula [2].

Examples of a salt of hydroxylamine include a hydrochloride salt and a sulfate salt.

The amount of hydroxylamine or its salt used may be 2 to 100-fold moles, preferably 2 to 20-fold moles, for the amount of the compound of the formula [2].

The reaction may be carried out at 0 to 150° C., preferably at 50 to 150° C. for 1 minute to 24 hours.

(2-2)

The compound of the general formula [7] may be produced by reacting the compound of the formula [6] with a reactive derivative or an alkylating agent in the presence or absence of a base.

A solvent used in the reaction is not particularly restricted, insofar as it does not adversely affect the reaction. Examples of the solvent include: amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitrites such as acetonitrile; sulfoxides such as dimethyl sulfoxide; ketones such as acetone and 2-butanone; esters such as ethyl acetate; carboxylic acids such as acetic acid; heteroaromatics such as pyridine; and water. These solvents may be used in combination.

Examples of the reactive derivative include: acid anhydrides such as acetylformyloxide, acetic anhydride, trichloroacetic anhydride and trifluoroacetic anhydride; mixed acid anhydrides of an organic carboxylic acid such as acetic acid, and monoalkyl esters of formic acid such as ethyl chloroformate and isobutyl chloroformate; mixed acid anhydrides of an organic carboxylic acid such as acetic acid, and organic acids such as pivalic acid; acid chlorides such as acetyl chloride, trichloroacetyl chloride and trifluoroacetyl chloride; acid bromides such as acetyl bromide; active esters such as p-nitrophenyl ester, N-hydroxysuccinimide ester and N-hydroxyphthalimide ester. These reactive derivatives may be used without isolation after preparation in the reaction system.

The reactive derivative may be prepared in the reaction system using a coupling reagent. Examples of a coupling reagent include: carbodiimides such as N,N'-dicyclohexylcarbodiimide and N-ethyl-N'-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; and O-(7-azabenzotriazol-1-yl)-1,1,3,3-tetramethyluronium hexafluorophosphate.

Examples of an alkylating agent include: alkyl halides such as methyl iodide or ethyl iodide; aralkyl halides such as benzyl chloride and benzyl bromide; and sulfate esters such as dimethyl sulfate.

Examples of a base, which may be optionally used in the reaction, include: metal alkoxides such as sodium methoxide, sodium ethoxide, potassium tert-butoxide and sodium tert-butoxide; inorganic bases such as sodium hydroxide, potassium hydroxide, sodium bicarbonate, sodium carbonate, potassium carbonate, sodium hydride and potassium hydride; and organic bases such as triethylamine and pyridine.

The amount of the reactive derivative, the alkylating agent and the base used may be 2 to 100-fold moles, preferably 2 to 10-fold moles, for the amount of the compound of the formula [6].

The reaction may be carried out at −20 to 100° C., preferably at 0 to 50° C. for 1 minute to 24 hours.

(2-3)

The compound of the formula [5] may be produced by subjecting the compound of the formula [6] to a reduction reaction. Additionally, the compound of the formula [5] may also be produced by subjecting the compound of the general formula [7] to a reduction reaction.

Examples of a reduction reaction used include a catalytic hydrogenation reaction using a metal catalyst, and a reduction using a metal and an acid, for example, zinc-acetic acid.

When the compound of the formula [6] or the compound of the general formula [7] is subjected to the catalytic hydrogenation reaction, a solvent used is not particularly restricted, insofar as it does not adversely affect the reaction. Examples of the solvent include: alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitrites such as acetonitrile; ketones such as acetone and 2-butanone; esters such as ethyl acetate; carboxylic acids such as acetic acid; heteroaromatics such as pyridine; and water. These solvents may be used in combination.

Examples of the metal catalyst include: palladium catalysts such as palladium on carbon, palladium oxide, palladium hydroxide and palladium black; nickel catalysts such as Raney nickel; and platinum oxide. The amount of the catalyst used may be 0.001 to 1-fold (W/W), preferably 0.01 to 0.5-fold (W/W), for the amount of the compound of the formula [6] or the compound of the general formula [7].

Examples of the reducing agent other than hydrogen include formic acid; formates such as sodium formate, ammonium formate and triethylammonium formate; cyclohexene; and cyclohexadiene. The amount of the agent used may be 2 to 100-fold moles, preferably 2 to 10-fold moles, for the amount of the compound of the formula [6] or the compound of the general formula [7].

The hydrogen pressure for the catalytic hydrogenation reaction of the compound of the formula [6] may be atmospheric pressure to 30 atm, preferably 2 to 10 atm.

The hydrogen pressure for the catalytic hydrogenation reaction of the compound of the general formula [7] may be atmospheric pressure.

The reaction may be carried out at 0 to 200° C., preferably at 0 to 100° C. for 1 minute to 24 hours.

(2-4)

The compound of the general formula [1] may be produced by subjecting the compound of the formula [5] to an alkoxycarbonylation reaction with a reactive derivative in the presence or absence of a base. The reaction may be conducted based on the production method 1-3.

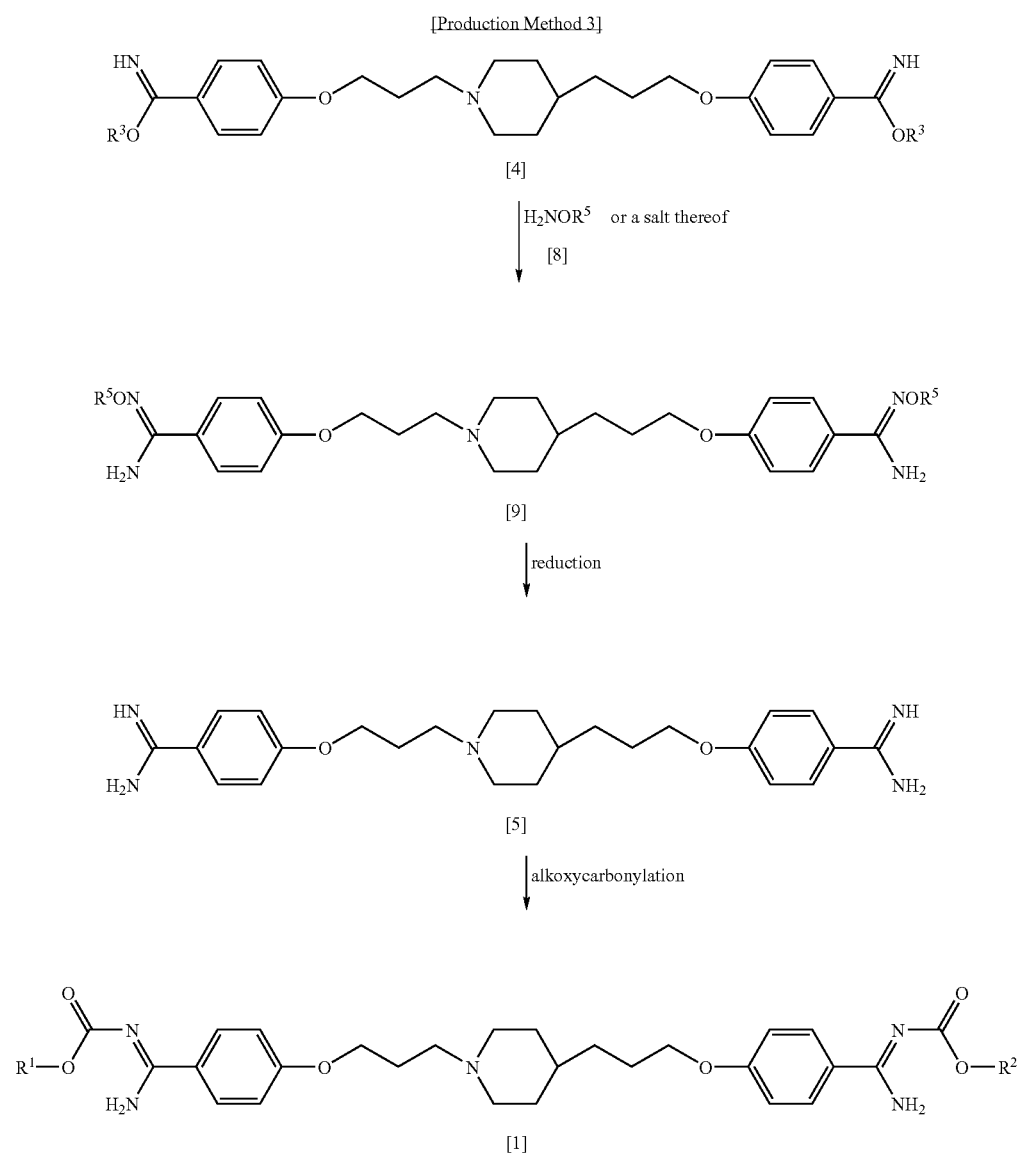

wherein R[5] represents a lower alkyl or aralkyl group which is optionally substituted; and R[1], R[2] and R[3] are as defined above.

The compound of the general formula [9] may be produced from the compound of the general formula [4]. By reducing the compound of the general formula [9], the compound of the formula [5] may be produced. Then, the compound of the formula [5] may be alkoxycarbonylated to produce the compound of the general formula [1].

Next, a series of these reactions is described below in detail.

(3-1)

The compound of the general formula [9] may be produced by reacting the compound of the general formula [4] with the compound of the general formula [8] or a salt thereof.

Examples of the compound of the general formula [8] include O-methylhydroxylamine and O-benzylhydroxylamine.

Examples of the salt of the compound of the general formula [8] include a hydrochloride salt and a sulfate salt.

The reaction may be conducted based on the production method 1-2.

(3-2)

The compound of the formula [5] may be produced by reducing the compound of the general formula [9]. The reaction may be conducted based on the production method 2-3.

(3-3)

The compound of the general formula [1] may be produced by subjecting the compound of the formula [5] to an alkoxycarbonylation reaction with a reactive derivative in the presence or absence of a base. The reaction may be conducted based on the production method 1-3.

In the above production methods, the compounds in states of solvates, hydrates and various forms of crystals may be used.

The production method of the compound of the formula [2], which is a raw material for the production of compounds of the present invention, is described below. The compound of the formula [2] may be produced by combining per se publicly known methods, for example, by the following production method.

[Production method A]

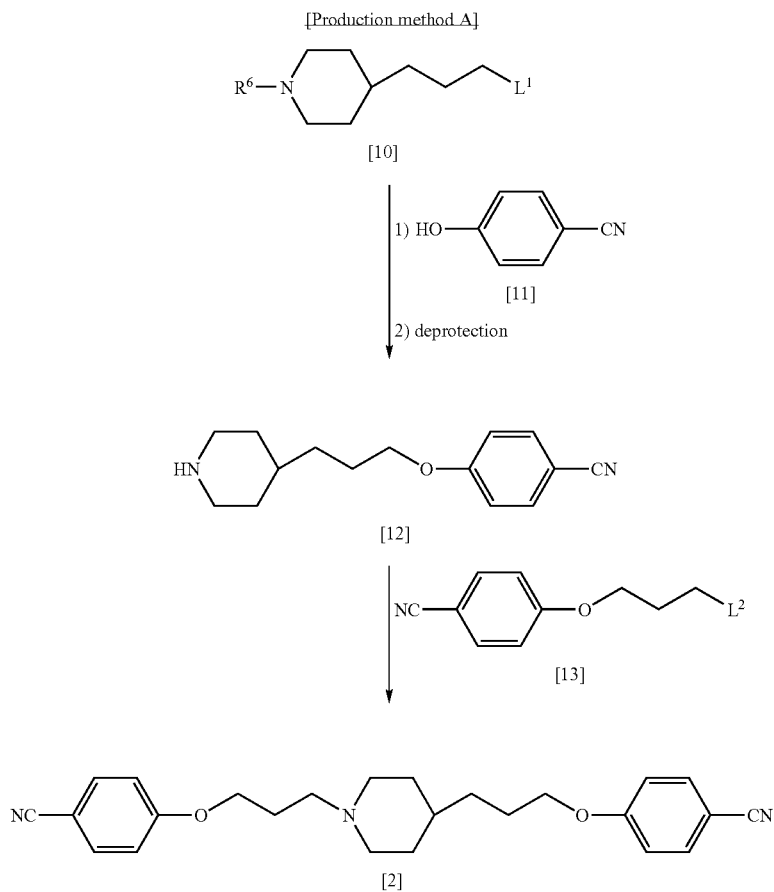

wherein $R^6$ represents an amino protecting group; and $L^1$ and $L^2$ stand for leaving groups.

Examples of the compound of the general formula [10] include benzyl 4-(3-bromopropyl)piperidine-1-carboxylate (J. Med. Chem., vol. 46, p. 2606-2620 (2003)), tert-butyl 4-(3-bromopropyl)-1-piperidinecarboxylate (Tetrahedron, vol. 55, p. 11619-11639 (1999)) and 3-[N-[(tert-butoxy)carbonyl]piperidin-4-yl]propyl iodide (J. Med. Chem., vol. 37, p. 2537-2551 (1994)). Further, the same may be synthesized using a raw material of tert-butyl 4-(3-hydroxypropyl)-1-piperidinecarboxylate, etc. by combining publicly known methods.

(A-1)

The compound of the formula [12] may be produced by reacting the compound of the general formula [10] with the compound of the formula [11] in the presence or absence of a base, followed by deprotection.

A solvent used in the reaction is not particularly restricted, insofar as it does not adversely affect the reaction. Examples of the solvent include: alcohols such as methanol, ethanol, 2-propanol and 2-methyl-2-propanol; amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitriles such as acetonitrile; sulfoxides such as dimethyl sulfoxide; ketones such as acetone and 2-butanone; esters such as ethyl acetate; heteroaromatics such as pyridine; and water. These solvents may be used in combination.

Examples of a base, which may be optionally used in the reaction, include: metal alkoxides such as sodium methoxide, sodium ethoxide, potassium tert-butoxide and sodium tert-butoxide; inorganic bases such as sodium hydroxide, potassium hydroxide, sodium bicarbonate, sodium carbonate, potassium carbonate, sodium hydride and potassium hydride; and organic bases such as triethylamine, N,N-diisopropylethylamine and pyridine.

The amount of the base used may be 1 to 10-fold moles, preferably 1 to 3-fold moles, for the amount of the compound of the general formula [10].

The amount of the compound of the formula [11] used may be 1 to 20-fold moles, preferably 1 to 5-fold moles, for the amount of the compound of the general formula [10].

The reaction may be carried out at 0 to 200° C., preferably at 0 to 150° C. for 1 minute to 24 hours.

Removal of the amino protecting group denoted as $R^6$ may be carried out in accordance with or based on a method described in "Protective groups in organic synthesis" (third edition, p. 494-653 (1999)) or the like.

(A-2)

The compound of the formula [2] may be produced by reacting the compound of the formula [12] with the compound of the general formula [13]. The reaction may be conducted according to the production method A-1.

[Production method B]

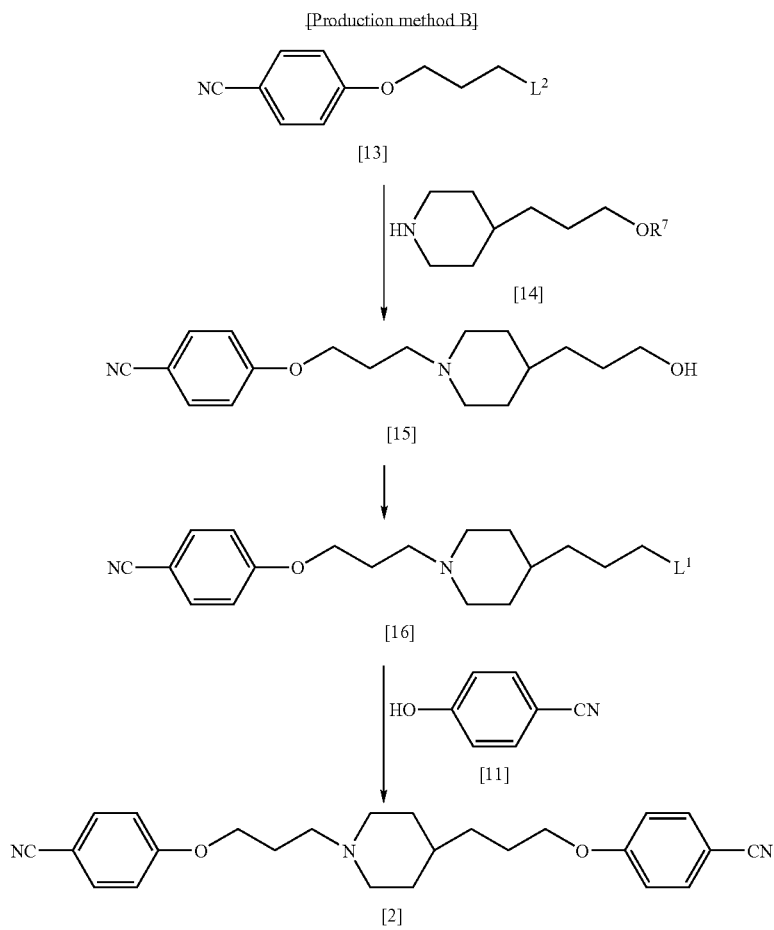

wherein $R^7$ represents a hydrogen atom or a hydroxyl protecting group; and $L^1$ and $L^2$ are as defined above.

As the compound of the general formula [14], 3-(4-piperidinyl)-1-propanol is known. Further, the compound of the general formula [14] may be produced by using as a raw material tert-butyl 4-(3-hydroxypropyl)-1-piperidinecarboxylate and the like, and combining publicly known methods.

(B-1)

The compound of the formula [15] may be produced by reacting the compound of the general formula [13] with the compound of the general formula [14], followed by deprotection, if necessary. The reaction may be conducted based on the production method A-1.

Removal of the hydroxyl protecting group denoted as $R^7$ may be carried out in accordance with or based on a method described in "Protective groups in organic synthesis" (third edition, p. 17-245 (1999)) or the like.

(B-2)

The compound of the general formula [16] may be produced by converting the hydroxyl group of the compound of the formula [15] to a leaving group.

When the leaving group is an alkanesulfonyloxy group or an arylsulfonyloxy group, the compound of the formula [15] may be reacted, in the presence or absence of a base, with an alkanesulfonyl chloride such as methanesulfonyl chloride, or an arylsulfonyl chloride such as p-toluenesulfonyl chloride.

Examples of a base which may be optionally used in the reaction, include: metal alkoxides such as sodium methoxide, sodium ethoxide, potassium tert-butoxide and sodium tert-butoxide; inorganic bases such as sodium hydroxide, potassium hydroxide, sodium bicarbonate, sodium carbonate, potassium carbonate, sodium hydride and potassium hydride; and organic bases such as triethylamine, N,N-diisopropylethylamine and pyridine.

The amount of the alkanesulfonyl chloride or the arylsulfonyl chloride as well as the base used may be 1 to 10-fold moles, preferably 1 to 3-fold moles, for the amount of the compound of the formula [15].

When the leaving group is a halogen atom, the compound of the formula [15] may be reacted with, for example, thionyl chloride, thionyl bromide, boron tribromide and carbon tetrabromide-triphenylphosphine.

The amount of such reagents used may be 1 to 10-fold moles, preferably 1 to 3-fold moles, for the amount of the compound of the formula [15].

A solvent used in the reaction is not particularly restricted, insofar as it does not adversely affect the reaction. Examples of the solvent include: amides such as N,N-dimethylformamide, N,N-dimethylacetamide and 1-methyl-2-pyrrolidone; halogenated hydrocarbons such as methylene chloride, chloroform and dichloroethane; aromatic hydrocarbons such as benzene, toluene and xylene; ethers such as dioxane, tetrahydrofuran, anisole, diethylene glycol dimethyl ether, diethylene glycol diethyl ether and ethylene glycol monomethyl ether; nitriles such as acetonitrile; sulfoxides such as dimethyl sulfoxide; and heteroaromatics such as pyridine. These solvents may be used in combination.

(B-3)

The compound of the formula [2] may be produced by reacting the compound of the general formula [16] with the compound of the formula [11]. The reaction may be conducted based on the production method A-1.

[Production method C]

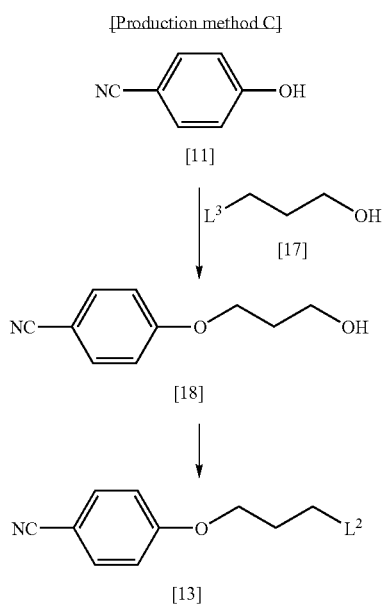

wherein L³ represents a leaving group; and L² is as defined above.

Examples of the compound of the general formula [17] include 3-chloro-1-propanol and 3-bromo-1-propanol.

(C-1)

The compound of the formula [18] may be produced by reacting the compound of the formula [11] with the compound of the general formula [17]. The reaction may be conducted based on the production method A-1.

(C-2)

The compound of the general formula [13] may be produced by converting the hydroxyl group of the compound of the formula [18] to a leaving group. The reaction may be conducted based on the production method B-2.

When the compound of the present invention is utilized as a medicine, formulation aids generally used for formulation, for example, an excipient, a carrier and a diluent, may be admixed appropriately. The medicine may be orally or parenterally administered in a usual manner in a form of a tablet, a capsule, a powder, a syrup, a granule, a pill, a suspension, an emulsion, a liquid, a powdered formulation, a suppository, an eyedrop, a nosedrop, an eardrop, a plaster, an ointment or an injection. The administration method, the dosage and the frequency of the administrations may also be selected appropriately depending on the age, body weight and symptoms of a patient. Generally, for an adult, a dose of 0.01 to 1,000 mg/kg per day may be administered, divided in 1 to several fractions, orally or parenterally (for example, by injection, drip infusion and rectal administration).

To elucidate the usefulness of the compound of the present invention, the following tests were conducted.

As Comparative Compounds, a compound described in Example 91 of WO-A-03-074476, and compounds described in Examples 32 and 33 of WO-A-2006-003881 were used.

Comparative Compound 1 (WO-A-03-074476, Example 91)

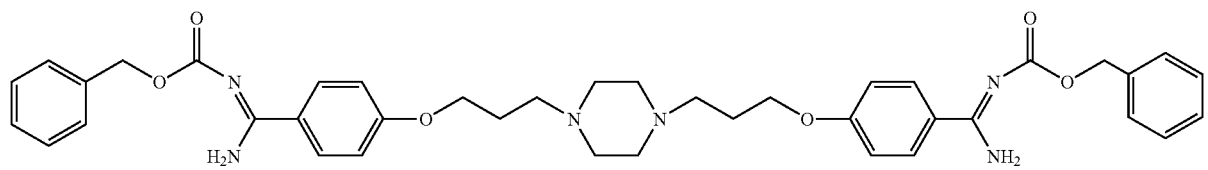 [SMILES: N/C(=N\C(=O)OCc1ccccc1)c1ccc(OCCCN2CCN(CCCOc3ccc(/C(N)=N/C(=O)OCc4ccccc4)cc3)CC2)cc1]

Comparative Compound 2 (WO-A-2006-003881, Example 32)

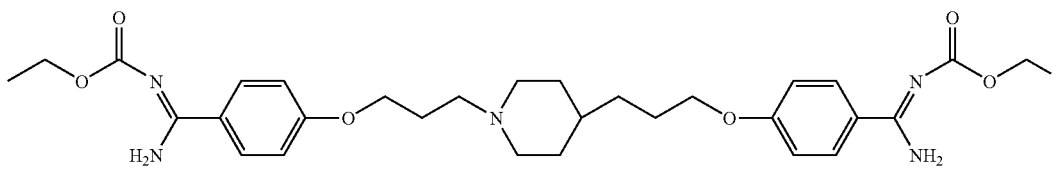 [SMILES: CCOC(=O)/N=C(\N)c1ccc(OCCCC2CCN(CCCOc3ccc(/C(N)=N/C(=O)OCC)cc3)CC2)cc1]

Comparative Compound 3 (WO-A-2006-003881, Example 33)

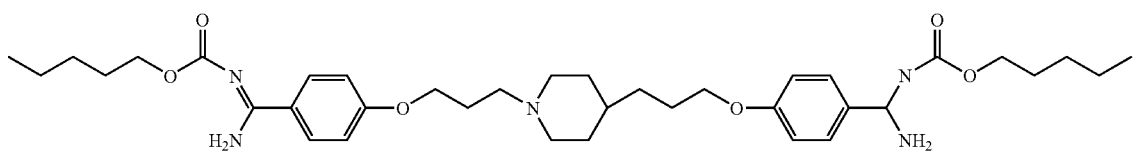 [SMILES: CCCCCOC(=O)/N=C(\N)c1ccc(OCCCN2CCC(CCCOc3ccc(C(N)NC(=O)OCCCCC)cc3)CC2)cc1]

Test Example 1

Test Using a Murine *Candida* Infection Model (Oral Administration)

As Test Compounds, the compounds of Example 1, Example 2, Example 3 and Example 4 were used.

*Candida albicans* TIMM 1623 was cultured at 35° C. overnight on a Sabouraud dextrose agar medium (SDA) plate, and the obtained culture was suspended in a sterile physiological saline solution, which was then diluted to prepare an inoculum solution.

Male mice (4 week-old, 5 mice/group) were administered intraperitoneally with 200 mg/kg of cyclophosphamide 4 days before infection and 100 mg/kg on the following day after the infection to obtain transient compromised condition. The prepared inoculum solution of *Candida albicans* TIMM 1623 in the amount of 0.2 mL was inoculated into the tail vein of each mouse to induce infection (about $3 \times 10^4$ CFU/mouse). The Test Compounds were dissolved in 0.1 mol/L hydrochloric acid, and the solution was diluted with sterile water and administered orally at the dose of 3 mg/kg body weight of mouse. This treatment was started 2 hours after the infection and conducted once daily for 7 days. To a group receiving no Test Compounds, an equal amount of a sterile physiological saline solution was administered. Viability of the mice was observed and recorded for 14 days after infection.

As a result, the mice in the group receiving no Test Compounds all died, while 80% or more of the mice in the groups receiving the compounds of Example 1, Example 2, Example 3 and Example 4 survived.

The compounds of Example 1, Example 2, Example 3 and Example 4 demonstrated excellent therapeutic efficacy.

Test Example 2

Test Using a Murine *Candida* Infection Model (Subcutaneous Administration)

As a Test Compound, the compound of Example 3 was used.

Male mice (4 week-old, 5 mice/group) were administered intraperitoneally with 200 mg/kg of cyclophosphamide 4 days before infection and 100 mg/kg on the following day after the infection to obtain transient compromised condition. *Candida albicans* TIMM 1623 cultured on SDA at 35° C. was suspended in a sterile physiological saline solution to prepare a suspension at $1.5 \times 10^5$ cells/mL. Each 0.2 mL of the solution was inoculated into the tail vein of each mouse to induce infection (about $3 \times 10^4$ CFU/mouse). The Test Compound was dissolved in a small amount of 0.1 mol/L hydrochloric acid, and the solution was diluted with a sterile physiological saline solution to obtain a 0.01 mg/mL solution. The solution was administered subcutaneously at the dose of 10 mL/kg body weight of mouse (0.1 mg/kg body weight). The administrations were conducted once 2 hours after the infection and once daily for the following consecutive 3 days, totaling 4 times. To a group receiving no Test Compound, an equal amount of a sterile physiological saline solution was administered. Viability of the mice was observed and recorded for 21 days after infection.

As a result, the mice in the group receiving no Test Compound all died, while 80% of the mice in the group receiving the compound of Example 3 survived.

The compound of Example 3 demonstrated excellent therapeutic efficacy.

Test Example 3

Test Using a Murine *Aspergillus* Infection Model (Oral Administration)

As Test Compounds, the compound of Example 3 and Comparative Compound 1 were used.

Spores of *Aspergillus fumigatus* IFM46895 were cultured on a potato dextrose agar medium at 30° C. for a week. The recovered spores were suspended in a sterile physiological saline solution containing 0.05% Tween 80, which was then diluted to prepare an inoculum solution.

Male mice (4 week-old, 5 mice/group) were administered intraperitoneally with 200 mg/kg of cyclophosphamide 4 days before infection and 100 mg/kg on the following day after the infection to obtain transient compromised condition. Each 0.2 mL of the inoculum solution was inoculated into the tail vein of each mouse to induce infection (about $1 \times 10^5$ CFU/mouse). The Test Compounds were dissolved in a small amount of 0.1 mol/L hydrochloric acid, and the solution was diluted with a sterile distilled water to obtain a 1 mg/mL solution. The solution was administered orally at the dose of 10 mL/kg body weight of mouse (10 mg/kg body weight). The administrations were conducted once 2 hours after the infection and once daily for the following 6 days, totaling 7 times. To a group receiving no Test Compounds, an equal amount of a sterile physiological saline solution was administered. Viability of the mice was observed and recorded for 21 days after infection.

As a result, the mice in the group receiving no Test Compound all died. 20% of the mice in the group receiving the Comparative Compound 1 survived, while 80% of the mice in the group receiving the compound of Example 3 survived.

The compound of Example 3 demonstrated excellent therapeutic efficacy.

Test Example 4

Test Using a Murine *Aspergillus* Infection Model (Subcutaneous Administration)

As a Test Compound, the compound of Example 3 was used.

Spores of *Aspergillus fumigatus* IFM46895 were cultured on a potato dextrose agar medium at 30° C. for a week. The recovered spores were suspended in a sterile physiological saline solution containing 0.05% Tween 80, which was then diluted to prepare an inoculum solution.

Male mice (4 week-old, 5 mice/group) were administered intraperitoneally with 200 mg/kg of cyclophosphamide 4 days before infection and 100 mg/kg on the following day after the infection to obtain transient compromised condition. Each 0.2 mL of the inoculum solution was inoculated into the tail vein of each mouse to induce infection (about $1 \times 10^5$ CFU/mouse). The Test Compound was dissolved in a small amount of 0.1 mol/L hydrochloric acid, and the solution was diluted with a sterile physiological saline solution to obtain a 0.03 mg/mL solution. The solution was administered subcutaneously at the dose of 10 mL/kg body weight of mouse (0.3 mg/kg body weight). The administrations were conducted once 2 hours after the infection and once daily for the following 6 days, totaling 7 times. To a group receiving no Test Compound, an equal amount of a sterile physiological saline solution was administered. Viability of the mice was observed and recorded for 21 days after infection.

As a result, the mice in the group receiving no Test Compound all died, while 60% of the mice in the group receiving the compound of Example 3 survived.

The compound of Example 3 demonstrated excellent therapeutic efficacy.

Test Example 5

Growth Inhibition Test on Vero Cells

As Test Compounds, the compounds of Example 1 and Example 2 and Comparative Compound 1 were used.

The cytotoxicity of the compounds was evaluated using Vero cells. The respective Test Compounds were dissolved in dimethylsulfoxide (DMSO) to prepare solutions at 10 mg/mL. The solutions were diluted with E'MEM with 10% FBS to a final concentration of 50 µg/mL and placed onto a 96-well plate. The cells were suspended in E'MEM with 10% FBS and seeded onto the 96-well plate at 3000 cells/well and then cultured in a $CO_2$ incubator at 37° C. for 3 days. The growth of Vero cells was evaluated by an assay using 2,3-bis-(2-methoxy-4-nitro-5-sulfophenyl)-5-[(phenylamino)carbonyl]-2H-tetrazolium (inner salt) monosodium salt ("XTT"). Namely, an XTT solution containing 1 mg/mL of XTT and 25 µmol/L of phenazine methosulfate (PMS) was added to each well. After incubating in a $CO_2$ incubator for 2 hours, the absorbance at 450 nm (reference at 655 nm) of the respective wells was measured by a microplate reader. The T/C (%) was calculated from the absorbance ratios of the control (without the Compound) and the respective wells. The results are shown in Table 1.

TABLE 1

| Test Compound | Cytotoxicity T/C (%) |
|---|---|
| Example 1 | 100 |
| Example 2 | 100 |
| Comparative Compound 1 | 1 |

A compound of the present invention was by far superior in safety to Comparative Compound 1.

Test Example 6

Repeated Intravenous Dose Toxicity Study in Mice

As Test Compounds, the compound of Example 3, Comparative Compound 2 and Comparative Compound 3 were used.

A repeated intravenous dose toxicity study was conducted using ICR strain male mice (6 week-old, 5 mice/group). The administration solutions were prepared by adding 3-fold molar amount of hydrochloric acid to the respective Test Compounds, and further adding a sterile physiological saline solution. The compounds of Example 3 and Comparative Compound 2, respectively at 25 mg/kg, and Comparative Compound 1 at 6.25 mg/kg were administered into the tail vein once daily for 3 days. To the control group, a sterile physiological saline solution was administered.

On day 1 after the completion of the administration, each mouse was etherized. Blood samples were taken from the abdominal vein using an injection syringe containing heparin as an anticoagulant (Novo-Heparin 1,000 units for injection, Aventis Pharma Ltd.), and the samples were centrifuged (3,300 rpm, 4° C., 10 min; Kubota Model 5900) to obtain the plasma. The blood biochemical tests with respect to aspartate aminotransferase (AST) and alanine aminotransferase (ALT) for the samples were conducted according to the JSCC consensus measuring method. The values for the Test Compounds and Comparative Compounds were calculated based on the values for the control (administration of a sterile physiological saline solution) as 100.

No abnormality in AST or ALT was observed for the compound of Example 3. On the other hand, by Comparative Compounds 2 and 3, increases in AST and ALT were observed, indicating occurrence of liver damages.

A compound of the present invention was superior in safety to Comparative Compound 2 and Comparative Compound 3.

Test Example 7

Acute Toxicity Study in Mice (Oral Administration)

A 100 mg/mL suspension of the compound of Example 3 was prepared with 0.1 mol/L hydrochloric acid. The Test Compound solution was orally administered to male mice (6 week-old, 2 mice/group) at 10 mL/kg (1000 mg/kg body weight) and the mice were observed until day 2 after administration.

As a result, all mice survived until day 2 after administration.

Test Example 8

Acute Toxicity Study in Mice (Intravenous Administration)

The compound of Example 3 was dissolved in a small amount of 0.1 mol/L hydrochloric acid, and the solution was diluted with a sterile physiological saline solution to obtain a 5 mg/mL solution. The Test Compound solution was administered intravenously to male mice (4 week-old, 2 mice/group) at 10 mL/kg (50 mg/kg body weight) and the mice were observed until day 2 after administration.

As a result, all mice survived until day 2 after administration.

Test Examples 7 and 8 demonstrated that a compound of the present invention was superior in safety.

Test Example 9

Inhibitory Effects on a Hepatic Drug-Metabolizing Enzyme in Humans (1) Inhibitory Effect on CYP2D6

Inhibitory effects of the compound of Example 3, Comparative Compound 1, Comparative Compound 2 and Comparative Compound 3 on human hepatic drug-metabolizing enzyme CYP2D6 were compared. A microsome prepared from insect cells expressing human CYP2D6 was used, and a substrate was 3-[2-(N,N-diethyl-N-methylammonium) ethyl]-7-methoxy-4-methylcoumarin iodide. The reaction was conducted in a phosphate buffer solution (100 mmol/L, pH 7.4) including final concentrations of 20 nmol/L for the enzyme, 1.5 µmol/L for the substrate, 1.55 mmol/L for nicotinamide adenine dinucleotide phosphate oxidized form (NADP+), 3.3 mmol/L for glucose-6-phosphate, 3.3 mmol/L for magnesium chloride and 0.4 Units/mL for glucose-6-phosphate dehydrogenase (G6PDH). The concentrations of the respective compounds in the reaction solution were prepared in a 3-fold dilution series with a final concentration range of 72 to 0.0329 µmol/L. The reaction solutions were incubated at 37° C. for 30 min. Then the reaction was terminated by a 80% acetonitrile solution (containing tris at a final concentration of 0.1 mol/L), and the enzyme activity was determined by measuring fluorescence with wavelength of 465 nm using excitation wavelength of 400 nm. The inhibitory effect was expressed as $IC_{50}$. Quinidine was used as a positive control.

The compound of Example 3 had no inhibitory effect on CYP2D6 up to 72 µmol/L. Comparative Compound 1, with $IC_{50}$ of 0.68 µmol/L, inhibited human CYP2D6 strongly. Comparative Compound 2 and Comparative Compound 3 inhibited human CYP2D6.

(2) Inhibitory Effect on CYP2C19

Inhibitory effects of the compound of Example 3 and Comparative Compound 1 on human hepatic drug-metabolizing enzyme CYP2C19 were compared. A microsome prepared from insect cells expressing human CYP2C19 was used. Dibenzylfluorescein was used as a substrate. The reaction was conducted in a phosphate buffer solution (100 mmol/L, pH 7.4) including final concentrations of 15 nmol/L for the enzyme, 1.0 µmol/L for the substrate, 1.55 mmol/L for nicotinamide adenine dinucleotide phosphate oxidized form (NADP+), 3.3 mmol/L for glucose-6-phosphate, 3.3 mmol/L for magnesium chloride and 0.4 Units/mL for glucose-6-phosphate dehydrogenase (G6PDH). The concentrations of the respective compounds in the reaction solution were prepared in a 3-fold dilution series with a final concentration range of 72 to 0.0329 µmol/L. The reaction solutions were incubated at 37° C. for 30 min. Then the reaction was terminated by a 2 mol/L sodium hydroxide aqueous solution, and the reactant was further incubated at 37° C. for 2 hours. The enzyme activity was determined by measuring fluorescence with wavelength of 535 nm using excitation wavelength of 485 nm. The inhibitory effect was represented as $IC_{50}$. Tranylcypromine was used as a positive control.

The compound of Example 3 had no effect on CYP2C19 activity at 72 µmol/L. While Comparative Compound 1 inhibited human CYP2C19 strongly with $IC_{50}$ of 4.36 µmol/L.

(3) Inhibitory Effect on CYP3A4

Inhibitory effects of the compound of Example 3 and Comparative Compound 1 on human hepatic drug-metabolizing enzyme CYP3A4 were compared. A microsome prepared from insect cells expressing human CYP3A4 was used. Dibenzylfluorescein was used as a substrate. The reaction was conducted in a phosphate buffer solution (100 mmol/L, pH 7.4) including final concentrations of 2.5 nmol/L for the enzyme, 1.0 µmol/L for the substrate, 1.55 mmol/L for nicotinamide adenine dinucleotide phosphate oxidized form (NADP+), 3.3 mmol/L for glucose-6-phosphate, 3.3 mmol/L for magnesium chloride and 0.4 Units/mL for glucose-6-phosphate dehydrogenase (G6PDH). The concentrations of the respective compounds in the reaction solution were prepared in a 3-fold dilution series with a final concentration range of 72 to 0.0329 µmol/L. The reaction solutions were incubated at 37° C. for 15 min. Then the reaction was terminated by a 2 mol/L sodium hydroxide aqueous solution, and the solution was further incubated at 37° C. for 2 hours. The enzyme activity was determined by measuring fluorescence with wavelength of 535 nm using excitation wavelength of 485 nm. The inhibitory effect was expressed as $IC_{50}$. Clotrimazole was used as a positive control.

The compound of Example 3, with the $IC_{50}$ of 45.4 µmol/L, inhibited human CYP3A4 weakly. While Comparative Compound 1 inhibited human CYP3A4 strongly with $IC_{50}$ of 4.73 µmol/L.

A compound of the present invention showed weak Inhibitory effect on various hepatic drug-metabolizing enzymes, having limited drug interaction risk with other agents, and were superior in safety compared to the comparative compounds.

EXAMPLES

The present invention will now be described by way of Reference Examples and Examples, but the present invention should not be limited thereto.

Hereinafter, the mixing ratio of an eluent is always expressed in a volume ratio, and a support of column chromatography is BW Silica Gel BW-127ZH (Fuji Silysia Chemical Ltd.), unless otherwise specified.

The abbreviations in Examples have the following meanings respectively:

Ac: acetyl, Me: methyl, Ms: methanesulfonyl, DMSO-$d_6$: deuterated dimethyl sulfoxide.

Reference Example 1

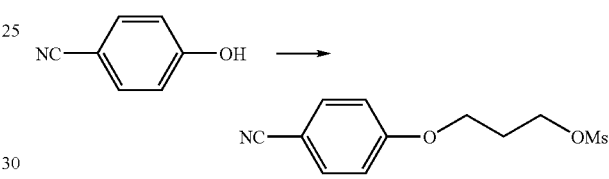

Into a suspension of 9.42 g of potassium tert-butoxide in 100 mL of N,N-dimethylformamide, 10.0 g of 4-cyanophenol and 7.02 mL of 3-chloro-1-propanol were added under water-cooling, and the suspension was stirred at 100° C. for 1 hour. To the reaction mixture, after being cooled to room temperature, 200 mL of water and 200 mL of ethyl acetate were added. The organic layer was separated, washed with a 5% potassium carbonate aqueous solution and a saturated sodium chloride aqueous solution successively, and dried over anhydrous magnesium sulfate, followed by solvent removal by evaporation under reduced pressure. The obtained oily substance 11.9 g was dissolved in 100 mL of dioxane. To the mixture 9.28 mL of triethylamine was added, and 5.15 mL of methanesulfonyl chloride was dropped under cooling on ice over 8 min, which was then stirred at room temperature for 10 min. The reaction mixture, after dropping 100 mL of water, was stirred at room temperature for 45 min. The solid matter was collected by filtration and washed with 100 mL of water and 50 mL of 2-propanol to obtain 12.3 g of 3-(4-cyanophenoxy)propyl methanesulfonate as a white solid.

$^1$H-NMR (CDCl$_3$) δ: 2.27 (2H, tt, J=6.0, 6.0 Hz), 3.02 (3H, s), 4.15 (2H, t, J=6.0 Hz), 4.45 (2H, t, J=6.0 Hz), 6.93-6.99 (2H, m), 7.57-7.61 (2H, m).

Reference Example 2

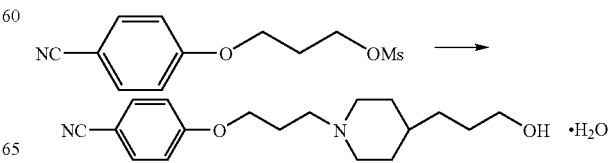

Into a solution of 50.0 g of 3-(4-cyanophenoxy)propyl methanesulfonate in 250 mL of N,N-dimethylformamide, 32.5 g of potassium iodide, 32.9 g of sodium bicarbonate and 37.0 g of 3-(4-piperidinyl)-1-propanol hydrochloride were added at room temperature, which was then stirred at 70° C. for 7 hours. To the reaction mixture, after being cooled down to room temperature, 250 mL of water and 150 mL of toluene were added, and then hydrochloric acid was added to adjust the pH to 1.0. The aqueous layer was separated, adjusted to pH 10.0 with a 20% sodium hydroxide aqueous solution, and stirred at room temperature for 15 min and under cooling on ice for 30 min. The solid matter was collected by filtration and washed twice with 50 mL of water and twice with 50 mL of toluene to obtain 52.3 g of 4-{3-[4-(3-hydroxypropyl)-1-piperidinyl]propoxy}benzonitrile monohydrate as a white solid.

$^1$H-NMR (CDCl$_3$) δ: 1.20-1.75 (10H, m), 1.85-2.05 (4H, m), 2.46-2.50 (2H, m), 2.90-2.94 (2H, m), 3.64 (2H, t, J=6.6 Hz), 4.06 (2H, t, J=6.3 Hz), 6.92-6.96 (2H, m), 7.55-7.59 (2H, m).

Reference Example 3

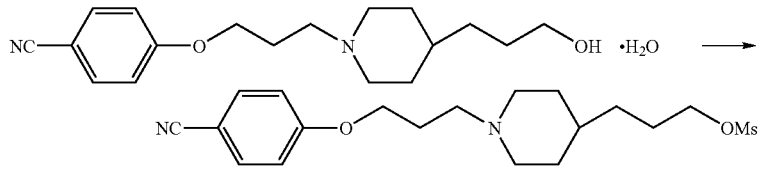

A solution of 96.2 g of 4-{3-[4-(3-hydroxypropyl)-1-piperidinyl]propoxy}benzonitrile monohydrate in 870 mL of tetrahydrofuran was heated to evaporate off 480 mL of tetrahydrofuran under atmospheric pressure. To the solution, 36.4 g of triethylamine was added under water-cooling, then 36.1 g of methanesulfonyl chloride was dropped over 10 min, and the solution was stirred at room temperature for 20 min. After adding 6.07 g of triethylamine and 6.87 g of methanesulfonyl chloride, the solution was stirred at room temperature for 20 min, to which 3.03 g of triethylamine and 3.44 g of methanesulfonyl chloride were additionally added, and the solution was stirred at room temperature for 20 min. To the solution 192 mL of 2-propanol was then added, and 670 mL of water was dropped over 25 min under cooling on ice. After stirring at the same temperature for 30 min, the solid matter was collected by filtration, and washed twice with 100 mL of a 50% (V/V) 2-propanol aqueous solution to obtain 93.4 g of 3-{1-[3-(4-cyanophenoxy)propyl]-4-piperidinyl}propyl methanesulfonate as a white solid.

$^1$H-NMR (CDCl$_3$) δ: 1.18-1.38 (5H, m), 1.55-1.82 (4H, m), 1.88-2.05 (4H, m), 2.44-2.52 (2H, m), 2.88-2.96 (2H, m), 3.01 (3H, s), 4.06 (2H, t, J=6.3 Hz), 4.22 (2H, t, J=6.6 Hz), 6.92-6.96 (2H, m), 7.56-7.59 (2H, m).

Reference Example 4

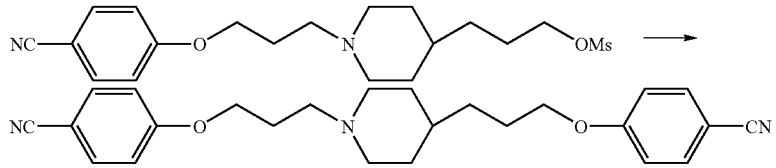

Into a solution of 91.9 g of 3-{1-[3-(4-cyanophenoxy)propyl]-4-piperidinyl}propyl methanesulfonate in 460 mL of dimethylsulfoxide, 66.9 g of potassium carbonate and 28.8 g of 4-cyanophenol were added at room temperature, and the solution was stirred at 60° C. for 2 hours. To the reaction mixture, after being cooled down to room temperature, 640 mL of water was dropped over 20 min, and then the mixture was stirred at room temperature for 35 min, and under water cooling for 30 min. The solid matter was collected by filtration, and washed twice with 180 mL of water and then 360 mL of 2-propanol to obtain 90.0 g of 4-(3-{4-[3-(4-cyanophe $^1$H-NMR (CDCl$_3$) δ: 1.20-1.45 (5H, m), 1.65-2.05 (8H, m), 2.40-2.55 (2H, m), 2.85-3.00 (2H, m), 3.99 (2H, t, J=6.5 Hz), 4.06 (2H, t, J=6.3 Hz), 6.93 (2H, d, J=8.8 Hz), 6.94 (2H, d, J=8.8 Hz), 7.57 (2H, d, J=8.8 Hz), 7.57 (2H, d, J=8.8 Hz).

Reference Example 5

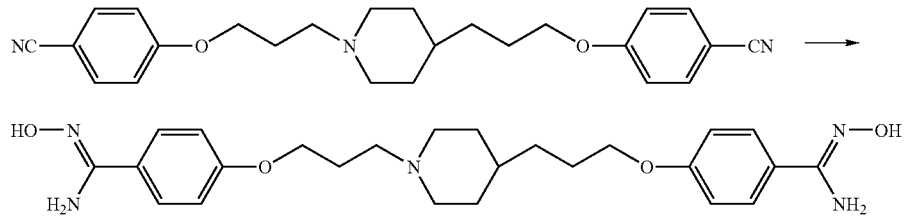

Into a suspension of 12.6 g of 4-(3-{4-[3-(4-cyanophenoxy)propyl]-1-piperidinyl}propoxy)benzonitrile in 126 mL of dimethylsulfoxide, 19.1 mL of a 50% hydroxylamine aqueous solution was added, and the suspension was stirred at 50° C. for 19 hours. To the mixture, after being cooled down to room temperature, 260 mL of water was dropped over 50 min, which was then stirred at room temperature for 30 min and under water cooling for 2 hours. The solid matter was collected by filtration to obtain 15.0 g of 4-{3-[4-(3-{4-[amino(hydroxyimino)methyl]phenoxy}propyl)-1-piperidinyl]propoxy}-N'-hydroxybenzamidine as a white solid.

$^1$H-NMR (DMSO-d$_6$) δ: 1.05-1.40 (5H, m), 1.60-1.80 (4H, m), 1.80-1.90 (4H, m), 2.35-2.45 (2H, m), 2.80-2.90 (2H, m), 3.96 (2H, t, J=6.5 Hz), 4.01 (2H, t, J=6.5 Hz), 5.65-5.75 (4H, m), 6.85-6.95 (4H, m), 7.55-7.65 (4H, m), 9.43 (1H, s), 9.43 (1H, s).

Reference Example 6

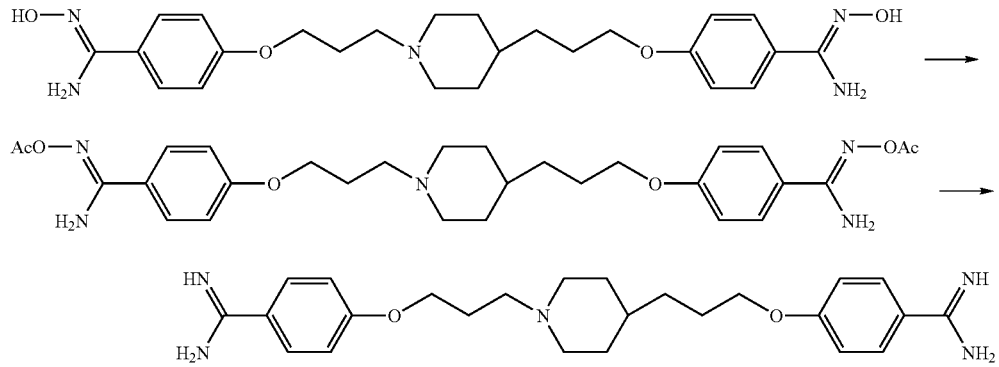

Into a suspension of 1.07 g of 4-{3-[4-(3-{4-[amino(hydroxyimino)methyl]phenoxy}propyl)-1-piperidinyl]propoxy}-N'-hydroxybenzamidine in 10 mL of acetic acid, 0.64 mL of acetic anhydride was added at room temperature, and the suspension was stirred at room temperature for 40 min. The mixture, after adding 0.10 g of 5% palladium on carbon, was stirred under hydrogen atmosphere for 2 hours 15 min. The mixture was filtered to remove insoluble matters, and after adding 4 mL of 6.0 mol/L hydrochloric acid, the mixture was filtered again to remove insoluble matters, and the solvent was removed by evaporation under reduced pressure. To the obtained residue, a 5.0 mol/L sodium hydroxide aqueous solution was added to adjust the pH to 12.5, then the solid matter was collected by filtration to obtain 0.61 g of 4-{3-[4-(3-{4-[amino(imino)methyl]phenoxy}propyl)-1-piperidinyl]propoxy}benzamidine as a white solid.

$^1$H-NMR (DMSO-d$_6$) δ: 1.00-1.40 (5H, m), 1.60-1.80 (4H, m), 1.80-1.95 (4H, m), 2.35-2.45 (2H, m), 2.80-2.90 (2H, m), 3.98 (2H, t, J=6.5 Hz), 4.03 (2H, t, J=6.3 Hz), 6.30-7.20 (4H, broad), 6.85-7.00 (4H, m), 7.65-7.80 (4H, m).

Reference Example 7

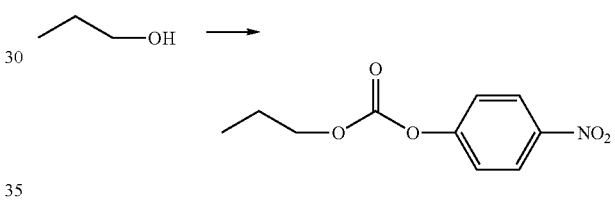

Into a solution of 0.75 g of propanol and 1.90 mL of triethylamine in 10 mL of tetrahydrofuran, a solution of 2.50 g of 4-nitrophenyl chloroformate in 15 mL of tetrahydrofuran was dropped under cooling on ice. After stirring at room temperature for 20 min, ethyl acetate and water were added to the reaction mixture. The organic layer was separated, washed with water and a saturated sodium chloride aqueous solution successively, dried over anhydrous magnesium sulfate, followed by solvent removal by evaporation under reduced pressure. To the residue, hexane was added, and insoluble matters were removed by filtration. After removing the solvent by evaporation under reduced pressure, 2.59 g of 4-nitrophenyl propyl carbonate was obtained as a light yellow oily matter.

¹H-NMR (CDCl₃) δ: 1.03 (3H, t, J=7.4 Hz), 1.71-1.85 (2H, m), 4.26 (2H, t, J=6.7 Hz), 7.39 (2H, d, J=9.0 Hz), 8.28 (2H, d, J=9.0 Hz)

Reference Example 8

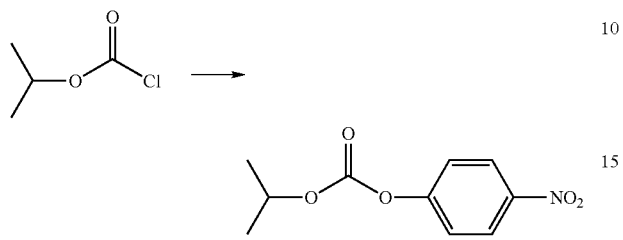

Into a solution of 3.00 g of 4-nitrophenol and 3.31 mL of triethylamine in 30 mL of tetrahydrofuran, 2.46 mL of isopropyl chloroformate was dropped under cooling on ice. To the reaction mixture, after stirred at the same temperature for 10 min, ethyl acetate and water were added. The organic layer was separated, washed with a saturated sodium chloride aqueous solution, dried over anhydrous magnesium sulfate, followed by solvent removal by evaporation under reduced pressure. The residue was dissolved in 50 mL of ethyl acetate, washed with a 5% potassium carbonate aqueous solution and a saturated sodium chloride aqueous solution successively and dried over anhydrous magnesium sulfate. After removing the solvent by evaporation under reduced pressure, 3.00 g of 4-nitrophenyl isopropyl carbonate was obtained as a light yellow solid.

¹H-NMR (CDCl₃) δ: 1.41 (6H, d, J=6.3 Hz), 4.96-5.07 (1H, m), 7.36-7.41 (2H, m), 8.25-8.30 (2H, m).

Reference Example 9

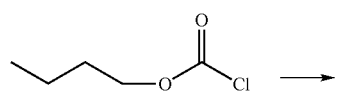

-continued

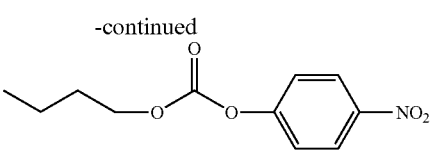

Into a solution of 3.00 g of 4-nitrophenol and 3.31 mL of triethylamine in 30 mL of tetrahydrofuran, 2.75 mL of butyl chloroformate was dropped under cooling on ice. To the reaction mixture, after stirred at the same temperature for 10 min, ethyl acetate and water were added. The organic layer was separated, washed with a saturated sodium chloride aqueous solution, and dried over anhydrous magnesium sulfate. After removing the solvent by evaporation under reduced pressure, 4.60 g of butyl 4-nitrophenyl carbonate was obtained as a light yellow oily matter.

¹H-NMR (CDCl₃) δ: 0.99 (3H, t, J=7.4 Hz), 1.41-1.52 (2H, m), 1.70-1.80 (2H, m), 4.30 (2H, t, J=6.6 Hz), 7.36-7.41 (2H, m), 8.26-8.31 (2H, m).

Reference Example 10

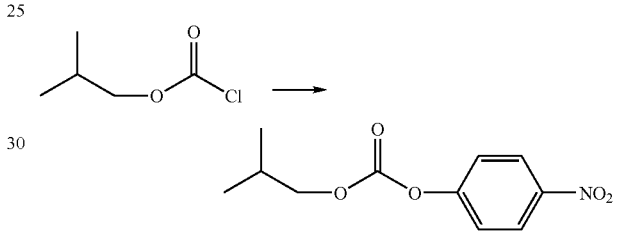

Similarly to Reference Example 9, from 3.00 g of 4-nitrophenol and 2.80 mL of isobutyl chloroformate, 5.63 g of isobutyl 4-nitrophenyl carbonate was obtained as a light yellow oily matter.

¹H-NMR (CDCl₃) δ: 1.02 (6H, d, J=6.6 Hz), 2.02-2.13 (1H, m), 4.08 (2H, d, J=6.6 Hz), 7.39 (2H, d, J=9.1 Hz), 8.28 (2H, d, J=9.1 Hz).

Example 1

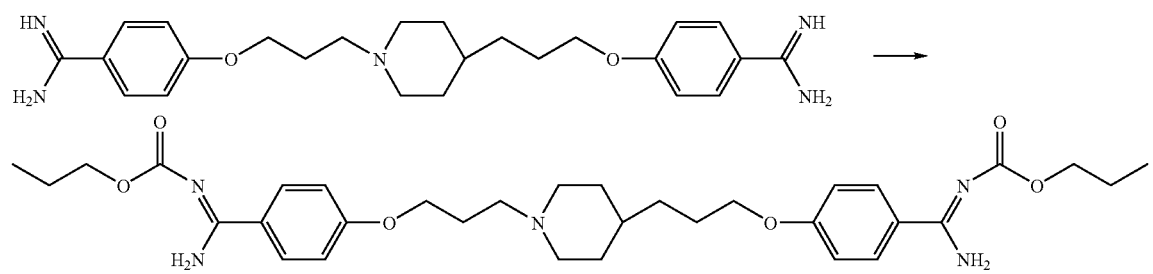

Into a solution of 1.71 g of 4-nitrophenyl propyl carbonate in 15 mL of N,N-dimethylformamide, 1.50 g of 4-{3-[4-(3-{4-[amino(imino)methyl]phenoxy}propyl)-1-piperidinyl]propoxy}benzamidine was added at room temperature, and the solution was stirred at the same temperature for 4 hours. Chloroform and water were added to the reaction mixture.

The organic layer was separated, washed with water, twice with a 5% potassium carbonate aqueous solution and with a saturated sodium chloride aqueous solution successively, and dried over anhydrous magnesium sulfate, followed by solvent removal by evaporation under reduced pressure. The obtained residue was purified by a silica gel column chromatography (eluent; chloroform:methanol=4:1). The obtained solid substance was dissolved in chloroform, washed with a 5% potassium carbonate aqueous solution and a saturated sodium chloride aqueous solution successively, and dried over anhydrous magnesium sulfate. After removing the solvent by evaporation under reduced pressure, 1.25 g of 4-{3-[4-(3-{4-[amino(propoxycarbonylimino)methyl]phenoxy}propyl)-1-piperidinyl]propoxy}-N'-(propoxycarbonyl)benzamidine was obtained as a white solid.

$^1$H-NMR (CDCl$_3$) δ: 0.99 (6H, t, J=7.4 Hz), 1.22-1.45 (5H, m), 1.66-1.86 (8H, m), 1.90-2.04 (4H, m), 2.46-2.54 (2H, m), 2.90-2.98 (2H, m), 3.99 (2H, t, J=6.5 Hz), 4.06 (2H, t, J=6.3 Hz), 4.11 (4H, t, J=7.0 Hz), 6.88-6.96 (4H, m), 7.82-7.88 (4H, m).

Example 2

Similarly to Example 1, from 1.82 g of butyl 4-nitrophenyl carbonate and 1.50 g of 4-{3-[4-(3-{4-[amino(imino)methyl]phenoxy}propyl)-1-piperidinyl]propoxy}benzamidine, 1.39 g of 4-{3-[4-(3-{4-[amino(butoxycarbonylimino)methyl]phenoxy}propyl)-1-piperidinyl]propoxy}-N'-(butoxycarbonyl)benzamidine was obtained as a white solid.

$^1$H-NMR (CDCl$_3$) δ: 0.95 (6H, t, J=7.3 Hz), 1.20-1.50 (9H, m), 1.60-2.05 (12H, m), 2.45-2.54 (2H, m), 2.90-3.00 (2H, m), 3.99 (2H, t, J=6.6 Hz), 4.06 (2H, t, J=6.3 Hz), 4.16 (4H, t, J=6.8 Hz), 6.88-6.96 (4H, m), 7.82-7.88 (4H, m).

Example 3-2

Into a solution of 1.82 g of butyl 4-nitrophenyl carbonate in 15 mL of N,N-dimethylformamide, 1.50 g of 4-{3-[4-(3-{4-[amino(imino)methyl]phenoxy}propyl)-1-piperidinyl]propoxy}benzamidine was added at room temperature, and the solution was stirred at the same temperature for 2 hours. Chloroform and water were added to the reaction mixture. The organic layer was separated, washed twice with a 5% potassium carbonate aqueous solution and with a saturated sodium chloride aqueous solution successively, and dried over anhydrous magnesium sulfate, followed by solvent

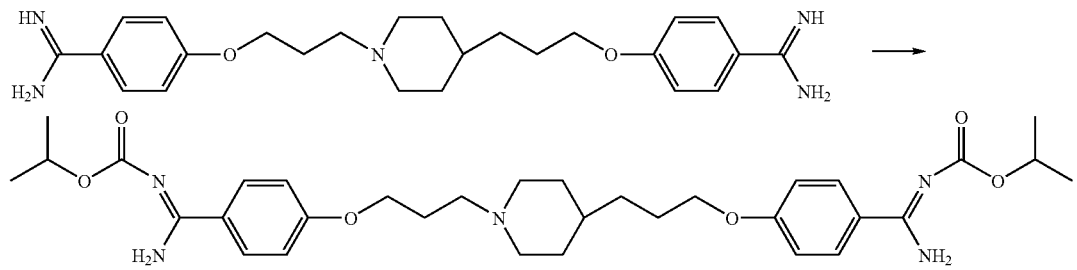

Similarly to Example 1, from 1.71 g of 4-nitrophenyl isopropyl carbonate and 1.50 g of 4-{3-[4-(3-{4-[amino(imino)methyl]phenoxy}propyl)-1-piperidinyl]propoxy}benzamidine, 1.35 g of 4-{3-[4-(3-{4-[amino(isopropoxycarbonylimino)methyl]phenoxy}propyl)-1-piperidinyl]propoxy}-N'-(isopropoxycarbonyl)benzamidine was obtained as a white solid.

$^1$H-NMR (CDCl$_3$) δ: 1.20-1.46 (5H, m), 1.34 (12H, d, J=6.3 Hz), 1.56-1.86 (4H, m), 1.88-2.04 (4H, m), 2.46-2.54 (2H, m), 2.90-2.98 (2H, m), 3.99 (2H, t, J=6.5 Hz), 4.06 (2H, t, J=6.3 Hz), 4.94-5.04 (2H, m), 6.88-6.96 (4H, m), 7.80-7.88 (4H, m).

Example 3-1 removal by evaporation under reduced pressure. The obtained residue was purified by a silica gel column chromatography (eluent; chloroform:methanol=4:1). The obtained solid substance was dissolved in chloroform, washed twice with a 5% potassium carbonate aqueous solution and with a saturated sodium chloride aqueous solution successively, and dried over anhydrous magnesium sulfate. After removing the solvent by evaporation under reduced pressure, 1.39 g of 4-{3-[4-(3-{4-[amino(butoxycarbonylimino)methyl]phenoxy}propyl)-1-piperidinyl]propoxy}-N'-(butoxycarbonyl)benzamidine was obtained as a white solid.

$^1$H-NMR (CDCl$_3$) δ: 0.95 (6H, t, J=7.3 Hz), 1.20-1.50 (9H, m), 1.60-2.05 (12H, m), 2.45-2.54 (2H, m), 2.90-3.00 (2H, m), 3.99 (2H, t, J=6.6 Hz), 4.06 (2H, t, J=6.3 Hz), 4.16 (4H, t, J=6.8 Hz), 6.88-6.96 (4H, m), 7.82-7.88 (4H, m).

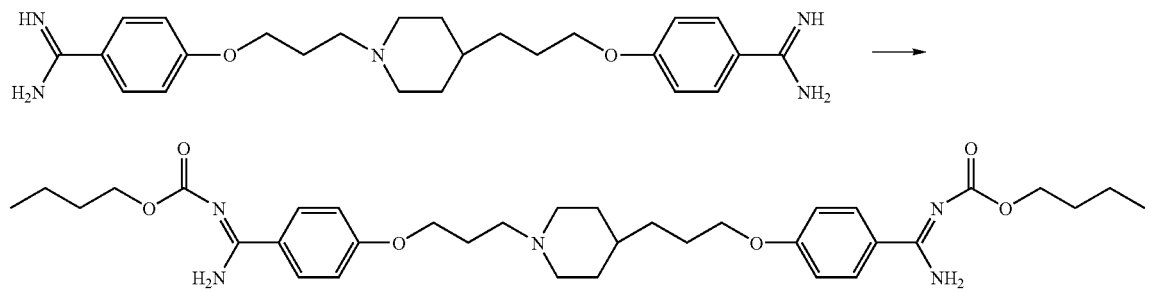

Example 4

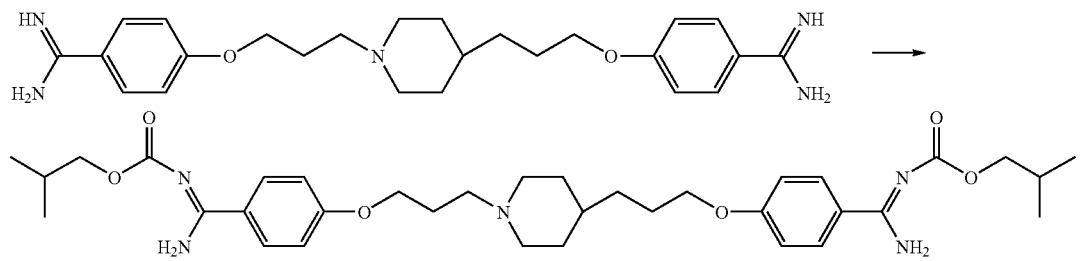

Into a solution of 1.82 g of isobutyl 4-nitrophenyl carbonate in 15 mL of N,N-dimethylformamide, 1.50 g of 4-{3-[4-(3-{4-[amino(imino)methyl]phenoxy}propyl)-1-piperidinyl]propoxy}benzamidine was added at room temperature, and the solution was left reacting at the same temperature for 17 hours. Chloroform and water were added to the reaction mixture. The organic layer was separated, washed with water, a 5% potassium carbonate aqueous solution and a saturated sodium chloride aqueous solution successively, and dried over anhydrous magnesium sulfate, followed by solvent removal by evaporation under reduced pressure. The obtained residue was purified by a silica gel column chromatography (eluent; chloroform:methanol=4:1). The obtained residue was dissolved in chloroform, washed with a 5% potassium carbonate aqueous solution and a saturated sodium chloride aqueous solution successively, and dried over anhydrous magnesium sulfate. After removing the solvent by evaporation under reduced pressure, 1.43 g of 4-{3-[4-(3-{4-[amino(isobutoxycarbonylimino)methyl]phenoxy}propyl)-1-piperidinyl]propoxy}-N'-(isobutoxycarbonyl)benzamidine was obtained as a white solid.

$^1$H-NMR (CDCl$_3$) δ: 0.99 (12H, d, J=6.8 Hz), 1.20-1.45 (5H, m), 1.55-2.12 (10H, m), 2.46-2.53 (2H, m), 2.90-3.00 (2H, m), 3.94 (4H, d, J=6.8 Hz), 3.99 (2H, t, J=6.5 Hz), 4.06 (2H, t, J=6.3 Hz), 6.88-6.96 (4H, m), 7.80-7.90 (4H, m).

Formulation Example 1

100 mg of the compound obtained in Example 1 and 18 g of sodium chloride were added to 1.8 L of water for injection. The pH was adjusted to 4 by hydrochloric acid. After dissolving the compound, water for injection was added to make 2 L. The solution was filtered through a membrane filter of 0.22 μm, and 100 mL of the obtained solution was filled and sealed in an ampule to obtain an injection.

Formulation Example 2

The mixture of 500 mg of the compound obtained in Example 1, 350 mg of lactose, 250 mg of corn starch and 400 mg of crystalline cellulose (trade name: Ceolus PH101, Asahi Kasei Chemicals Corp.), 0.6 mL of a 5% hydroxypropylcellulose aqueous solution and water were added, and the mixture was kneaded. The obtained mixture was dried at 60° C. and admixed with 100 mg of crospovidone (trade name: Kollidon CL, BASF), 100 mg of light anhydrous silicic acid and 20 mg of magnesium stearate. A tablet with a round-shaped and the diameter of 8 mm was obtained by compressing 175 mg of the mixture.

Formulation Example 3

The mixture of 500 mg of the compound obtained in Example 1, 200 mg of lactose and 530 mg of corn starch, 0.6 mL of a 5% hydroxypropylcellulose aqueous solution and water were added, and the mixture was kneaded. The obtained mixture was dried at 60° C. and admixed with 70 mg of crospovidone (trade name: Kollidon CL, BASF), 180 mg of crystalline cellulose (trade name: Ceolus PH302, Asahi Kasei Chemicals Corp.) and 20 mg of magnesium stearate. Into a gelatin capsule Type 3, 150 mg of the mixture was filled to obtain the encapsulated formulation.

INDUSTRIAL APPLICABILITY

Compounds of the present invention have a strong activity against fungi including azole-agent-resistant fungi, good oral absorption property and high safety, and therefore are useful as antifungal agents.

The invention claimed is:

1. 4-{3-[4-(3-{4-[amino(propoxycarbonylimino)methyl]phenoxy}propyl)-1-piperidinyl]propoxy}-N'-(propoxycarbonyl)benzamidine or a salt thereof.

2. 4-{3-[4-(3-{4-[amino(isopropoxycarbonylimino)methyl]phenoxy}propyl)-1-piperidinyl]propoxy}-N'-(isopropoxycarbonyl)benzamidine or a salt thereof.

3. 4-{3-[4-(3-{4-[amino(butoxycarbonylimino)methyl]phenoxy}propyl)-1-piperidinyl]propoxy}-N'-(butoxycarbonyl)benzamidine or a salt thereof.

* * * * *